United States Patent [19]

Watts et al.

[11] Patent Number: 4,843,847

[45] Date of Patent: Jul. 4, 1989

[54] APPARATUS AND METHOD FOR ULTRASONICALLY INSPECTING ARTICLES FOR INTERNAL DEFECTS

[75] Inventors: Kenneth C. Watts; Leslie T. Russell; Gregory R. Jollimore, all of Nova Scotia, Canada

[73] Assignee: Canadian Patents and Development Limited, Ottawa, Canada

[21] Appl. No.: 70,186

[22] Filed: Jul. 6, 1987

[30] Foreign Application Priority Data

Jul. 7, 1986 [CA] Canada .................................. 513207

[51] Int. Cl.$^4$ ............................................. G01N 29/04
[52] U.S. Cl. ........................................ 73/598; 73/600
[58] Field of Search ...................................209/590, 555; 73/597, 598, 599, 600, 621, 623, 644; 128/660

[56] References Cited

U.S. PATENT DOCUMENTS

| | | | |
|---|---|---|---|
| 2,768,524 | 10/1956 | Beard ..................................... | 73/599 |
| 3,435,950 | 4/1969 | Suverkrop ............................ | 209/590 |
| 3,546,498 | 12/1970 | McMaster et al. .................. | 310/325 |
| 3,908,445 | 9/1975 | Verdon et al. ........................ | 73/644 |
| 4,249,660 | 2/1981 | Woodland ............................ | 209/555 |
| 4,625,555 | 12/1986 | Fujii ..................................... | 73/598 |

OTHER PUBLICATIONS

Birth, G. S., American Potato Journal, "A Nondestructive Technique for Detecting Internal Discolorations in Potatoes", vol. 37, pp. 53–60, (1960).

Primary Examiner—Stewart J. Levy
Assistant Examiner—Robert Bell
Attorney, Agent, or Firm—Perry Carvellas

[57] ABSTRACT

A mechanically amplified electroacoustic transducer system comprising an electroacoustic transducer having a vibrating element and an amplifier rod forming a probe extending from the transducer and in acoustically coupling contact with the vibrating element over a relatively small region thereof. The probe has a length which is approximately equal to the quarter wavelength or a multiple of the quarter wavelength of the acoustical energy generated by the transducer, the exact length of the probe being selected to provide optimum output from the system at a selected operation frequency of the transducer. The invention also provides a method for detecting internal defects in an object which comprises placing the object between one or more transmitting electroacoustic transducer systems and a plurality of receiving electroacoustic transducer systems, each transducer system being as described above, bringing the tips of the transducer probes into contact with the object, energizing the or each transmitting transducer, obtaining electrical output signals from the receiving transducers, and determining from the amplitude or phase differences between the output signals the presence or absence of defects. The apparatus and method are especially suited to the detection of "hollow hearts" in potatoes.

16 Claims, 3 Drawing Sheets

APPARATUS AND METHOD FOR ULTRASONICALLY INSPECTING ARTICLES FOR INTERNAL DEFECTS

This invention relates to a method and apparatus for the detection of internal defects in various articles and is especially useful for detection of voids in lossy materials, such as potatoes.

Potato farmers in some years experience a crop condition in which these physiologically formed holes or voids-commonly known as "hollow hearts"-occur in the centers of the potatoes. If more than a certain percentage of the potatoes in a bin are found to have hollow hearts, the whole bin can be condemned as unfit for sale-even though the remaining potatoes may be whole. Clearly, therefore, it would be advantageous to have the means to economically and reliably detect potatoes with hollow hearts and, having removed them from the bin, be reasonably assured that the remaining potatoes are whole and fit for sale.

A relatively crude method involves the size sorting of the potatoes. Because hollow hearts usually occur during a period of rapid growth, a predominance of larger potatoes have hollow hearts. On a purely statistical basis, therefore, removing all the larger potatoes should reduce the incidence of hollow hearts. However, it has been found that a large proportion of the crop must be discarded to ensure that more than the minimum allowable percentage of potatoes is free from hollow hearts. Clearly, this is not an economically effective means of removing hollow heart potatoes from a field lot.

Another proposed method involves selection on the basis of specific gravity. Logically, if a hollow heart exists in a potato, the specific gravity should be less than a whole potato. However, workers have found that no well-defined value of specific gravity is apparent at which hollow hearts begin or cease to exist, although there are more hollow heart potatoes in lower specific gravity classes. The reason for this poor definition is that there is considerable variation in the specific gravity of various parts of the potato. Moreover, the practical difficulties of making specific gravity measurements without immersing the potatoes in water make this method unacceptable for commercial use.

Light transmittance and reflectance methods have both been used to detect imperfections in potatoes. Insofar as the detection of hollow heart is concerned, the most promising method of this type involves the use of a wide-range spectrophotometer specifically designed for recording spectral absorption curves of biological materials on a linear or logarithmic energy scale (Birth, G. S. 1960, "A Nondestructive Technique for Detecting Internal Discolorations in Potatoes"; Am. Potato J. 37:53–60). Because this method detects differences in colour, black spot and greening are also detected. However, if the hollow heart is not discoloured to any great extent, the instrument will not detect the defect. The absorption characteristics of the potato skin are similar to the absorption characteristics of the discolouration associated with hollow heart. Therefore, the size of the potato is found to be a factor in that the path length of the light through the skin constitutes a larger proportion of the total path length for small potatoes than large potatoes. Other variables that affect the measurement and may cause errors are variation in the spectral absorption of the skin, presence of scarred tissues, and soil on the tubers.

X-rays have been used to detect hollow hearts and a modified airport X-ray machine is currently in use on Prince Edward Island. However, this technology has the disadvantage that it only gives a visual indication; the defective tubers have to be extracted by hand; the cost of X-ray machinery is prohibitive for small potato farmers; and there are well-documented potential dangers in using X-rays on a regular basis.

Ultrasonic testing for hollow hearts has been the subject of considerable interest in that it is relatively safe, non-invasive to the material under test, and (by comparison with X-ray diagnosis, for example) relatively inexpensive. In order to maintain signal distortion to a minimum, the transducer thickness to diameter ratio must be kept to a value considerably less than unity. However, to achieve a point application of sound-which is essential for detection of small voids-the transducer diameter (and, hence, its thickness) must be made relatively small, which has led workers to employ frequencies in excess of 1 MHz. Attempts to use commercially available ultrasonic testing equipment which operates above 1 megahertz have been unsuccessful in that the high frequencies are unable to pass through potatoes. This is due to the structure of the potatoes in which interconnected air cells surround the fluid filled cells of the material. These air cells scatter and, hence, attenuate sound to a significant extent at the high frequencies that are necessary in good acoustic materials to obtain good resolution of the flaw.

Contrary to the findings of previous workers using ultrasonic techniques, we have found that for lossy media, such as potatoes, resolution of flaw detail can be accomplished at much lower frequencies than those used in commercial ultrasonic systems, if the sound energy is supplied to the potatoes over a reduced surface area.

Thus, it is an object of the present invention to provide an ultrasonic method and apparatus for detection of internal defects such as voids, which utilizes much lower frequencies than those used in commercial ultrasonic systems but enables the sound energy to be supplied to the material over a sufficiently reduced surface area to provide good resolution. The invention is especially useful in (although by no means restricted to) the detection of defects in lossy materials, such as vegetables. According to the present invention, mechanical sound amplification is employed to increase the area density of the sound energy, whereby frequencies from 30 kHz to 100 kHz (preferably from 40 to 60 kHz) may be used. Increasing the area density of the sound energy provides the advantage of reduction in the area over which sound is imparted to the material and, thus, the minimum size of the voids which can be detected.

Considering again the example of the potato, because it is an acoustically lossy material, a "through-transmission" system is employed wherein the potato is placed between the transmitting transducer and receiving transducer array, rather than the usual "pulse-echo" method of transmitting and receiving pulses using a single transducer. The presence of a hollow heart may be detected by a decrease in the amplitude of the received signal or a phase difference technique may be employed.

The invention further contemplates the use of a novel method of electrically driving an electroacoustic transducer, which comprises applying thereto a high voltage over a range of frequencies generated by a sweep generator or digitally stepped by a computer driving a digitalto-frequency converter. The sweep range embraces the range of expected natural resonant frequencies of the overall systems comprising the transmitting and receiving transducers and the various objects to be tested. For a particular object under test, the electrical output signal from the receiving transducer (or transducers) will peak at a specific frequency of the drive voltage to the transmitting transducer or transducers. A peak detector is employed to apply only the peak output signals to a computer for processing such signals in a conventional manner to provide output data representative of the presence or absence of defects in the object under test. For a series of objects (for example, potatoes) being tested in sequence, this technique enables the optimum output to be processed for each potato, regardless of the slight differences between the natural resonant frequencies of the respective transducer/potato systems.

The invention also resides in a novel combination of transducer and mechanical amplifier which may be used in any application wherein it is required to increase the area density of sound energy supplied to an object under test. More particularly, the amplifier comprises a probe which is coupled to the transducer and the length of which is selected to be a multiple of the quarter wavelength of the acoustic energy generated by the transducer. The length is optimized by experimentation and matched to the operation frequency of the transducer and of the overall system, as well as the material from which the amplifier probe is manufactured. For improved acoustical coupling between the tip of the rod and the object under investigation, water or other liquid may be applied through a conduit in the probe which is connected to a liquid supply source. The probe is preferably in the form of a rod which has a base in the form of a flange at its end remote from the tip, this base being substantially smaller in area than the area of the transducer element. Thus, only the central region of the transducer element is contacted by the base of the rod, which minimizes the inertial constraint upon the vibration of the transducer element imposed by the mass of the rod. This is in contrast to the so-called "horn-coupled" device such as that of U.S. Pat. No. 4,173,725 (Asai et al), wherein the base of the probe is flared into a horn shape which covers an area equal to the transducer element. In Asai et al, the device utilizes the generation of forwardly and rearwardly directed waves and bringing the waves reflected from the rear of the transducer into phase with the forwardly directed sound waves. This requires precise tuning of the instrument, because any out-of-phase reflections will result in attenuation instead of reinforcement of the sound waves. By coupling the probe only to the centre of the vibrating element, as in our case, such rearwardly directed waves are negligible and the instrument design is accordingly much simpler. Also at the relatively low frequencies at which the device of our invention is especially useful, radial excitation of the transducer element may be employed (which enables the use of a conventional transducer element) and the coupling of the probe to only the centre of the vibrating element enables this to be effected without constraint upon the vibrating element. This would not be possible with the Asai et al device, where the probe base covers the entirety of the transducer element.

The invention will now be described further by way of example only and with reference to the accompanying drawings, wherein.

Figure 1:
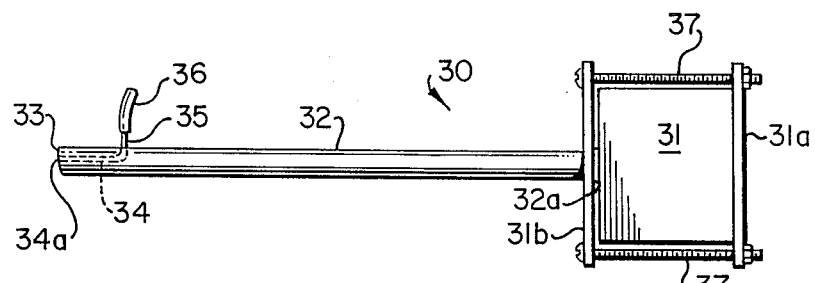
FIG. 1 is a side view of a transducer/amplifier combination in accordance with the present invention.

Referring to the drawings, and particularly to FIG. 1, there is shown in side elevation a transducer/amplifier combination 30 according to the invention. A conventional electro-acoustic transducer 31 is sandwiched between two plates 31a and 31b. Plate 31b has a central hole, through which passes a metal rod 32 which functions as a mechanical amplifier and as a probe for the transducer. The rod 32 has a small circular flange 31a at one end, which is sandwiched between plate 31b and the vibrating element of transducer 31 and which is just large enough to retain the rod in position. The plates 31a and 31b are clamped together by means of bolts 37. The degree of compression applied to flange 32a and transducer 31 is critical for maximum acoustic coupling therebetween and is adjusted by appropriate tightening of the bolts 37.

The length of the rod 32 is also somewhat critical and is selected to be a multiple of the wavelength of the acoustical energy emanating from the transducer. The precise length is determined by experimentation, since it is necessary to match the length to the operation frequency of the transducer, the frequency of operation of the system and the material of the rod 32.

The tip of the probe 32 is preferably slightly rounded rather than squared off to avoid damage to delicate or soft articles to which it is applied. Also, such a contour maximizes the contact area of the probe tip when it is applied to an article at an angle to perpendicular. The total deviation of the tip from square is preferably less than one twenty-fifth of the wavelength of the sound wave travelling through the probe in order to maintain negligible effect upon the natural resonance of the probe/transducer combination.

Good acoustical coupling between the probe tip 33 and the object under test is also critical. In ultrasonic testing, it is common to use a liquid (such as water) at the interface between the transducer and the object and even to immerse the object in a water bath. However, for the testing of vegetables such as potatoes, the application of a liquid over a significant area of the surface can be harmful to the object under test and, certainly, one could not use a water bath. Thus, we provide a means whereby water or other liquid is applied only at the point of contact between the probe tip 33 and the object under test. More particularly, a narrow conduit 34 is provided along the axis of the rod 32 and this conduit terminates at one end in a small orifice 34a at the probe tip and, at the other end, in a connection 35 for a liquid supply tube 36. It has been found in practice that the presence of a relatively narrow conduit (preferably having a cross-section of no more than about one fiftieth of the cross-sectional area of the rod) does not affect the sound field of the apparatus and the small orifice 34a ensures that water is applied precisely at the point of contact between the probe tip and the potato, where acoustical coupling is required.

The combination of transducer and mechanical amplifier according to the invention enables sound energy to be applied to an object under test over a greatly reduced surface area (i.e., the area of the probe tip 33) thus increasing the area density of the sound energy. Although the transducer size would still be in excess of 25 mm-much too large for direct application to an object wherein subsurface formations of only a few millimetres are to be located-the probe tip can be sufficiently small in area that this is not a problem. For example, in the testing of potatoes for hollow hearts as hereinafter described, voids as small as 3 mm in diameter can be detected.

A further significant advantage of this novel combination is that the transducer can be physically spaced from the object under test, since only the probe tip comes into contact with the surface.

Figure 2:
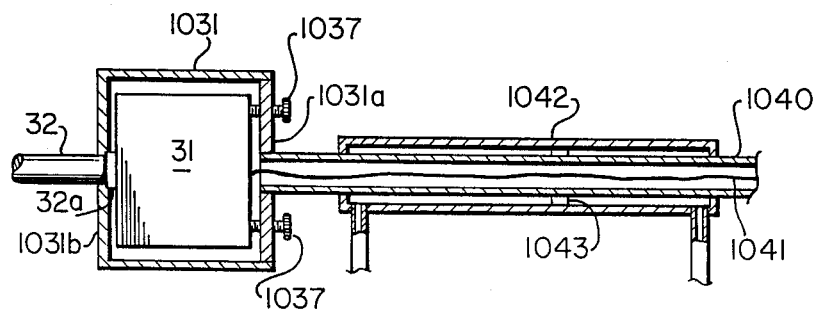
FIG. 2 is a side view of an alternative transducer mounting construction within the scope of the present invention.

FIG. 2 illustrates an alternative transducer mounting construction and also illustrates means for advancing and retracting the probe from the article under test. Rather than the plate 31b of FIG. 1, there is provided an aluminum bowl 1031, which effectively incorporates the plate 31b as its end face 1031b, having an aperture therethrough for the rod 32 in analogous manner to FIG. 1. The end plate 1031a is secured at its periphery (as by threaded engagement) to the bowl 1031 and load adjustment screws 1037 perform the function of the bolts 37 of FIG. 1. This construction has the advantage of providing a dust resistant enclosure for the transducer element 31.

The mounting of the transducer is effected by means of a hollow shaft 1040 rigidly secured to and extending rearwardly from a central aperture in the plate 1031a. The electrical wiring 1041 for the transducer is introduced through the hollow centre of the shaft. The shaft passes through a bi-directional pneumatic cylinder 1042 and is secured to the piston 1043 of the cylinder, so that the shaft can be moved axially from left to right in FIG. 2 by pneumatic pressure applied to the appropriate side of the piston 1043 in conventional fashion. This arrangement thereby enables support of the transducer, a conduit for the wiring to the transducer, and a means whereby the entire transducer assembly including the probe may be axially advanced and retracted towards and from the object under test.

Figure 3:
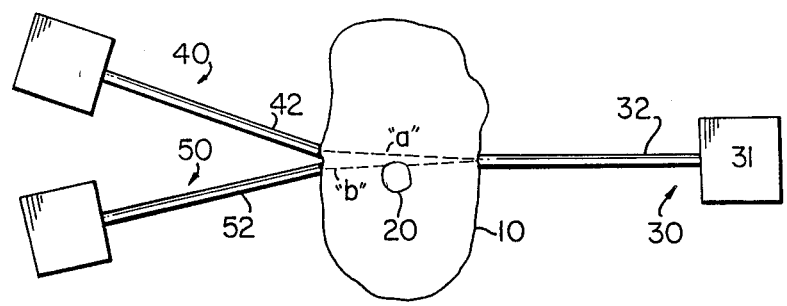
FIG. 3 is a schematic illustration of an arrangement for inspecting a potato for hollow hearts, using a plurality of transducer/amplifier combinations as shown in FIG. 1 or FIG. 2.

Referring now to FIG. 3, there is shown a potato 10 having a void 20. A transmitting transducer/amplifier 30 as described above, comprising transducer 31 and probe 32, is applied to one side of the potato with the tip of probe 32 in contact therewith. Water is applied to the interface between the rod and the potato as described in connection with FIG. 1. On the other side of the potato are positioned receiving transducer/amplifiers 40 and 50, which are identical to transducer/amplifier 30. The tips of the amplifier rods are placed as close together as possible, so that they are closely aligned with the probe 32 of transducer/amplifier 30. Again, water is injected through probes 42 and 52 to exit at the tips and improve the acoustic coupling with the potato.

Conventionally, the presence of a void would be detected by simply measuring the decrease in amplitude of the signal received by a single transducer. By using multiple transducers, as in FIG. 3, differential phase measurements can be employed. Such measurements are less sensitive to the contact resistance between the transducers and the potato but are dependent on the size of the hole and the thickness of the potato at any given point. Considering again FIG. 3, it may be seen that the potato happens to be positioned with the receiving transducers 40 and 50 approximately in line with the edge of void 20. The energy paths may be illustrated simplistically by means of dotted lines "a" and "b", and it will be seen that energy path "a" misses the void whilst energy path "b" passes through it. Thus, there is both an amplitude difference and a phase difference (due to the difference in time between the receipt of the signal by the two transducers) in the acoustical energy received by the respective transducers 40 and 50, due to the different conditions encountered by the respective energy paths.

Thus, if the potato is progressively moved into a series of positions between transmitter 30 and receivers 40 and 50, a "map" may effectively be obtained which not only shows the presence of a void or voids in the potato but also enables an estimation of their sizes.

Figure 6:
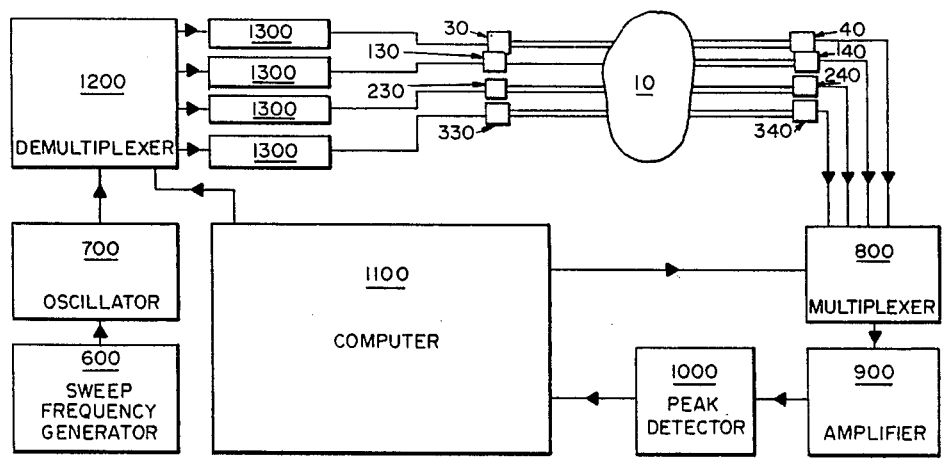
FIGS. 6 and 7 are block diagrams, including electrical circuitry, of further arrangements for inspection of potatoes or the like for subsurface defects.

A more convenient arrangement, using amplitude rather than phase difference measurements, is shown in FIG. 6. Considering the arrangement of FIG. 3 once again, it will be appreciated that for measurement of phase changes, the probe tips of the receivers must be close together, which effectively restricts the coverage to the energy paths "a" and "b" and necessitates the article to be progressively positioned as described above in order to obtain full coverage. The arrangement of FIG. 6 utilizes multiple transmitting and receiving probes 30, 130, 230, 330 and 40, 140, 240, 340, respectively. Thus, signals from each transmitter are picked up by the two or three receivers most nearly opposite-for example, signals from probe 30 may be picked up by receiving probes 40 and 140 whilst signals from probe 130 may be picked up by receiving probes 40, 140 and 240. By this means, it is possible to obtain multiple checks on hollows within the potatoes and to provide a greater area of coverage. Also, poor acoustical coupling for any probe may be detected and the results for that particular probe discarded.

Because only amplitude decrease is being measured in this arrangement, the probe tips need not be as close together as those of FIG. 3 for measurement purposes although, to satisfy regulatory authorities, for example, they may be closely spaced to ensure adequate resolution to detect very small voids. Thus, the spacing and number of probes required becomes a matter of choice dependent upon the minimum void size required to be detected.

Figure 4:
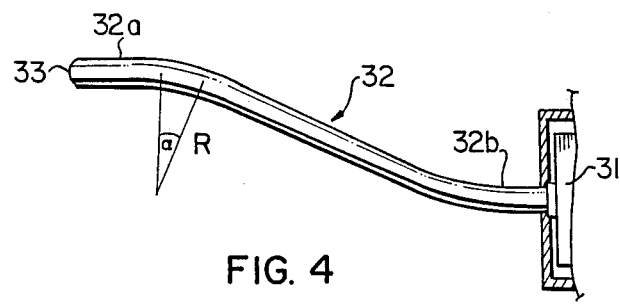
FIGS. 4 and 5 illustrate an alternative probe configuration within the scope of the present invention.
Figure 5:
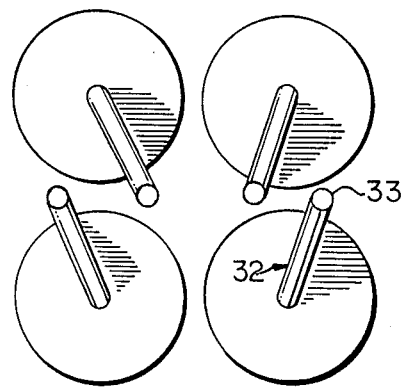

A means of enabling the probe tips to be closely spaced and still lie in a straight line, as well as allowing the transducer/rod assemblies to move parallel to one another, is illustrated in FIGS. 4 and 5. As may be seen, each rod is not straight but is formed with a gentle "S-bend", so that the tip region 32a is axially displaced from but substantially parallel to the base 32b of the rod adjacent the vibrating element 31. We have found that an angle of bend $\alpha$ (FIG. 4) of about 20° and a radius of curvature R of about five times the diameter of the rod, is preferred for best results. FIG. 5 clearly illustrates how four transducers can be clustered together whilst allowing the tips 33 to be maintained in a straight line, irrespective of the probe tip movement towards and away from the potato under test as dictated by the shape of the potato-which obviously varies from one sample to another.

FIG. 6 also illustrates, in purely schematic form, circuitry for driving the transducer/amplifier transmitters 30 through 330 and processing the signals received by receivers 40 through 340. The output of a sweep frequency generator 600 is applied to a low level voltage controlled oscillator 700. The signal generator drives class B transformer coupled amplifiers 1300 which provide a high voltage output within a frequency range from 30 to 100 kHz, the frequencies being swept around the expected optimum resonant frequency of the transducer/probe/potato system in order to maximize the output. The acoustic signals received by receivers 40 through 340 are converted to electrical signals which are applied to a multiplexer 800, and amplifier 900, peak detector 1000 and computer 1100. Computer 1100 drives multiplexer 800 and may also be used to drive a display or otherwise generate data relative to the presence or absence of voids within the potato. The computer may also operate ancillary equipment designed to further process the potato (e.g. reject or pass it on for packaging) dependent upon the test results.

A further function of computer 1100 is to drive a demultiplexer 1200, to which is applied the output from oscillator 700 and which applies the swept range of frequencies to amplifiers 1300.

The frequencies employed in this procedure are in the range of 30 to 100 kHz, but we prefer to use frequencies in the range of 40 to 60 kHz with a transducer having a natural frequency of about 200 kHz. However, transducers having natural frequencies from 100 to 500 kHz may be used, driven at suitably lower harmonic frequencies and connected to appropriately tuned probes.

The amplitude measurement (and, indeed, the measurement of phase differences in the arrangement of FIG. 3) and the determination therefrom of the presence of hollow hearts in the potato under test is effected by a computer (computer 1100 in the arrangement of FIG. 6) in a conventional manner, using an appropriate algorithm and associated hardware which do not form part of the present invention.

Figure 7:
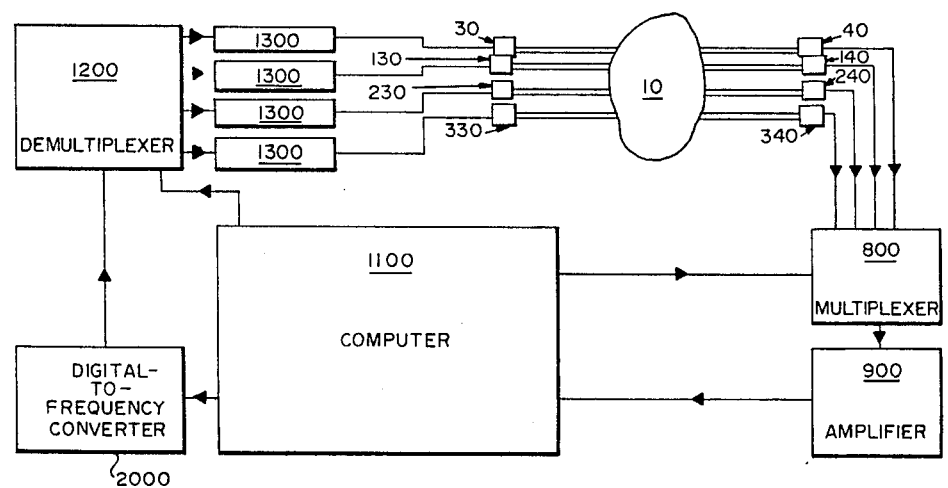

Alternative circuitry to that of FIG. 6 is shown in FIG. 7. With the exception of the following, the circuit of FIG. 7 operates in similar manner to that of FIG. 6. In the circuit of FIG. 7, computer 1100 sends a digital signal to a digital-to-frequency converter 2000, which in turn sends an analog signal to demultiplexer 1200. Thus, sweep frequency generator 600 and oscillator 700 of FIG. 6 are no longer required, since the frequencies are digitally stepped-albeit over the same range as that described in association with FIG. 6. Furthermore, the output voltages are stored in computer 1100 and the voltage peak is obtained by application of the software employed, rather than by use of the analog peak detector 1000 of FIG. 6. This circumvents any possible smoothing effect upon the data which may be caused by the analog peak detector circuitry.

We claim:

1. A method for detecting internal defects in a vegetable which comprises placing said vegetable between one or more transmitting electroacoustic transducer systems and a plurality of receiving electroacoustic transducer systems, each said transducer system comprising an electroacoustic transducer which has a probe extending therefrom forming a mechanical amplifier, bringing the tips of said probes into contact with said vegetable, energizing the or each said transmitting electroacoustic transducer system, obtaining electrical output signals from said receiving electroacoustic transducer systems, and determining from the amplitude or phase differences between said output signals the presence or absence of said defects.

2. A method for detecting hollow hearts in a potato, which comprises placing said potato between a transmitting electroacoustic transducer system and a pair of receiving electroacoustic transducer systems, each said transducer system comprising an electroacoustic transducer and an amplifying probe extending therefrom and acoustically coupled therewith, said probe having a length which is approximately equal to the quarter wavelength or a multiple of the quarter wavelength of the acoustical energy generated by said transducer, the exact length of said probe being selected to provide optimum output from said system at the operation frequency of said transducer; placing the tips of said receiving transducer probes close together against said potato and the tip of said transmitting transducer probe against the opposite side of said potato; transmitting an acoustic signal from said transmitting transducer through said potato and measuring the resulting electrical signals generated by said receiving transducers; measuring the phase difference between said electrical signals; and repeating the aforesaid operation over a plurality of cross-sections of said potato and determining from said phase difference measurements the presence of hollow hearts.

3. The method of claim 2, wherein each said probe is provided at its tip remote from said transducer with an orifice and a conduit through said probe communicating at one end with said orifice and at its opposite end with means for connection to a liquid supply source, said method further comprising the application of liquid to said potato through said conduit and said orifice to enhance the acoustical coupling between the probe and the potato surface.

4. A method for detecting hollow hearts in a potato, which comprises placing said potato between a plurality of transmitting electroacoustic transducer systems and a plurality of receiving electroacoustic transducer systems, each said transducer system comprising an electroacoustic transducer and a probe extending therefrom and acoustically coupled therewith, said probe forming a mechanical amplifier and having a length which is approximately equal to the quarter wavelength or a multiple of the quarter wavelength of the acoustical energy generated by said transducer, the exact length of said probe being selected to provide optimum output from said system at the operation frequency of said transducer; placing the tips of said receiving transducer probes against said potato in spaced apart relationship and the tips of said transmitting transducer probes against the opposite side of said potato in registry with the respective receiving transducer probes; transmitting acoustic signals from said transmitting transducer through said potato and measuring the resulting electrical signals generated by said receiving transducers; measuring amplitude differences between said electrical signals and determining therefrom the presence of hollow hearts.

5. The method of claim 4 wherein the amplifying probe of each said transducer system is formed with a gentle S-bend configuration with the tip region axially displaced from and substantially parallel to the base region of said probe adjacent said electroacousitc transducer.

6. A method for detecting hollow hearts in a potato which comprises placing said potato between one or more transmitting electroacoustic transducer systems and a plurality of receiving electroacoustic transducer systems, each said transducer system comprising an electroacoustic transducer which has a mechanically amplifying probe extending therefrom, bringing the tips of said probes into contact with said potato, energizing the or each said transmitting transducer, obtaining electrical output signals from said receiving transducers, and determining from the amplitude or phase differences between said output signals the presence or absence of said hollow hearts, wherein the or each said transmitting transducer is electrically driven by a high voltage over a range of frequencies, said frequencies being generated by a sweep generator and said frequency range embracing the natural resonant frequency to be expected from the acoustical system comprising the combination of the transducers and the potato under test; applying the electrical signals generated by said receiving transducers to peak detector means; applying detected peak signals from said peak detector means to computer means for effecting said measurements of phase difference or amplitude difference and determining therefrom the presence of hollow hearts.

7. A method for detecting hollow hearts in a potato, which comprises placing said potato between a transmitting electroacoustic transducer system and a pair of receiving electroacoustic transducer systems, each said transducer system comprising and electroacoustic transducer and an amplifying probe extending therefrom and acoustically coupled therewith, said probe having a length which is approximately equal to the quarter wavelength or a multiple of the quarter wavelength of the acoustical energy generated by said transducer, the exact length of said probe being selected to provide optimum output from said system at the operation frequency of said transducer; placing the tips of said receiving transducer probes close together against said potato and the tip of said transmitting transducer probe against the opposite side of said potato; transmitting an acoustic signal from said transmitting transducer through said potato and measuring the resulting electrical signals generated by said receiving transducers; measuring the phase difference between said electrical signals; and repeating the aforesaid operation over a plurality of cross-sections of said potato and determining from said phase difference measurements the presence of hollow hearts, wherein the or each said transmitting transducer is electrically driven by a high voltage over a range of frequencies, said frequencies being generated by a sweep generator and said frequency range embracing the natural resonant frequency to be expected from the acoustical system comprising the combination of the transducers and the potato under test; applying the electrical signals generated by said receiving transducers to peak detector means; applying detected peak signals from said peak detector means to computer means for effecting said measurements of phase difference or amplitude difference and determining therefrom the presence of hollow hearts.

8. The method of claim 7, wherein each said probe is provided at its tip remote from said transducer with an orifice and a conduit through said probe communicating at one end with said orifice and at its opposite end with means for connection to a liquid supply source, said method further comprising the application of liquid to said potato through said conduit and said orifice to enhance the acoustical coupling between the probe and the potato surface.

9. A method for detecting hollow hearts in a potato, which comprises placing said potato between a plurality of transmitting electroacoustic transducer systems and as plurality of receiving electroacoustic transducer systems, each said transducer system comprising an electroacoustic transducer and an amplifying probe extending therefrom and acoustically coupled therewith, said probe having a length which is approximately equal to the quarter wavelength or a multiple of the quarter wavelength of the acoustical energy generated by said transducer, the exact length of said probe being selected to provide optimum output from said system at the operation frequency of said transducer; placing the tips of said receiving transducer probes against said potato in spaced apart relationship and the tips of said transmitting transducer probes against the opposite side of said potato in registry with the respective receiving transducer probes; transmitting acoustic signals from said transmitting transducer through said potato and measuring the resulting electrical signals generated by said receiving transducers; measuring amplitude differences between said electrical signals and determining therefrom the presence of hollow hearts, wherein the or each said transmitting transducer is electrically driven by a high voltage over a range of frequencies, said frequencies being generated by a sweep generator and said frequency range embracing the natural resonant frequency to be expected from the acoustical system comprising the combination of the transducers and the potato under test; applying the electrical signals generated by said receiving transducers to peak detector means; applying detected peak signals from said peak detector means to computer means for effecting said measurements of phase difference or amplitude difference and determining therefrom the presence of hollow hearts.

10. The method of claim 9 wherein the amplifying probe of each said transducer system is formed with a gentle S-bend configuration with the tip region axially displaced from and substantially parallel to the base region of said probe adjacent said electroacoustic transducer.

11. A method for detecting hollow hearts in a potato which comprises placing said potato between one or more transmitting electroacoustic transducer systems and a plurality of receiving electroacoustic transducer systems, each said transducer system comprising an electroacoustic transducer which has a mechanically amplifying probe extending therefrom, bringing the tips of said probes into contact with said potato, energizing the or each said transmitting transducer, obtaining electrical output signals from said receiving transducers, and determining from the amplitude or phase differences between said output signals the presence or absence of said hollow hearts, wherein the or each said transmitting transducer is electrically driven by a high voltage over a range of frequencies, said frequencies being digitally generated by a computer feeding a digital to frequency converter and said frequency range embracing the natural resonant frequency to be expected from the acoustical system comprising the combination of the transducers and the potato under test; applying the electrical signals generated by said receiving transducers to computer means for detecting peak voltages of said signals and effecting said measurements of phase difference or amplitude difference and determining therefrom the presence of hollow hearts.

12. A method for detecting hollow hearts in a potato, which comprises placing said potato between a transmitting electroacoustic transducer system and a pair of receiving electroacoustic transducer systems, each said transducer system comprising an electroacoustic transducer and an amplifying probe extending therefrom and acoustically coupled therewith, said probe having a length which is approximately equal to the quarter wavelength or a multiple of the quarter wavelength of the acoustical energy generated by said transducer, the exact length of said probe being selected to provide optimum output from said system at the operation frequency of said transducer; placing the tips of said receiving transducer probes close together against said potato and the tip of said transmitting transducer probe against the opposite side of said potato; transmitting an acoustic signal from said transmitting transducer through said potato and measuring the resulting electrical signals generated by said receiving transducers; measuring the phase difference between said electrical signals; and repeating the aforesaid operation over a plurality of cross-sections of said potato and determining from said phase difference measurements the presence of hollow hearts, wherein the or each said transmitting transducer is electrically driven by a high voltage over a range of frequencies, said frequencies being digitally generated by a computer feeding a digital to frequency converter and said frequency range embracing the natural resonant frequency to be expected from the acoustical system comprising the combination of the transducers and the potato under test; applying the electrical signals generated by said receiving transducers to computer means for detecting peak voltages of said signals and effecting said measurements of phase difference or amplitude difference and determining therefrom the presence of hollow hearts.

13. The method of claim 12, wherein each said probe is provided at its tip remote from said transducer with an orifice and a conduit through said probe communicating at one end with said orifice and at its opposite end with means for connection to a liquid supply source, said method further comprising the application of liquid to said potato through said conduit and said orifice to enhance the acoustical coupling between the probe and the potato surface.

14. A method for detecting hollow hearts in a potato, which comprises placing said potato between a plurality of transmitting electroacoustic transducer systems and as plurality of receiving electroacoustic transducer systems, each said transducer system comprising an electroacoustic transducer and an amplifying probe extending therefrom and acoustically coupled therewith, said probe having a length which is approximately equal to the quarter wavelength or a multiple of the quarter wavelength of the acoustical energy generated by said transducer, the exact length of said probe being selected to provide optimum output from said system at the operation frequency of said transducer; placing the tips of said receiving transducer probes against said potato in spaced apart relationship and the tips of said transmitting transducer probes against the opposite side of said potato in registry with the respective receiving transducer probes; transmitting acoustic signals from said transmitting transducer through said potato and measuring the resulting electrical signals generated by said receiving transducers; measuring amplitude differences between said electrical signals and determining therefrom the presence of hollow hearts, wherein the or each said transmitting transducer is electrically driven by a high voltage over a range of frequencies, said frequencies being digitally generated by a computer feeding a digital to frequency converter and said frequency range embracing the natural resonant frequency to be expected from the acoustical system comprising the combination of the transducers and the potato under test; applying the electrical signals generated by said receiving transducers to computer means for detecting peak voltages of said signals and effecting said measurements of phase difference or amplitude difference and determining therefrom the presence of hollow hearts.

15. The method of claim 14 wherein the amplifying probe of each said transducer system is formed with a gentle S-bend configuration with the tip region axially displaced from and substantially parallel to the base region of said probe adjacent said electroacoustic transducer.

16. A method for detecting hollow hearts in a potato which comprises placing said potato between one or more transmitting electroacoustic transducer systems and a plurality of receiving electroacoustic transducer systems, each said transducer system comprising an electroacoustic transducer which has a probe extending therefrom forming a mechanical amplifier, bringing the tips of said probes into contact with said potato, energizing the or each said transmitting electroacoustic transmitting system, obtaining electrical output signals from said receiving electroacoustic transducer systems, and determining from the amplitude or phase difference between said output signals the presence or absence of said hollow hearts.

* * * * *